United States Patent
Makino et al.

(10) Patent No.: US 11,946,034 B2
(45) Date of Patent: Apr. 2, 2024

(54) STERILE SAMPLING APPARATUS

(71) Applicant: NIHON KOHDEN CORPORATION, Tokyo (JP)

(72) Inventors: Hodaka Makino, Tokorozawa (JP); Hirotsugu Kubo, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 926 days.

(21) Appl. No.: 16/932,957

(22) Filed: Jul. 20, 2020

(65) Prior Publication Data
US 2021/0024869 A1    Jan. 28, 2021

(30) Foreign Application Priority Data
Jul. 25, 2019    (JP) ................ 2019-137233

(51) Int. Cl.
| | |
|---|---|
| C12M 1/32 | (2006.01) |
| C12M 1/12 | (2006.01) |
| G01N 1/18 | (2006.01) |
| G01N 1/26 | (2006.01) |
| G01N 1/10 | (2006.01) |
| G01N 1/20 | (2006.01) |

(52) U.S. Cl.
CPC ............ *C12M 37/00* (2013.01); *C12M 33/06* (2013.01); *G01N 1/18* (2013.01); *G01N 1/26* (2013.01); *G01N 2001/1056* (2013.01); *G01N 2001/205* (2013.01)

(58) Field of Classification Search
CPC ...... C12M 33/06; C12M 37/00; C12M 33/00; G01N 1/18; G01N 1/26; G01N 2001/1056
See application file for complete search history.

(56) References Cited

U.S. PATENT DOCUMENTS

| | | | | |
|---|---|---|---|---|
| 4,942,770 A | * | 7/1990 | Seifert | ............... G01N 1/14 73/864.34 |
| 2004/0259241 A1 | * | 12/2004 | Barringer, Jr. | ... G01N 27/44704 435/286.5 |
| 2007/0128087 A1 | * | 6/2007 | Cannizzaro | ............ C12M 33/04 422/50 |
| 2008/0308494 A1 | * | 12/2008 | Barringer, Jr. | ............ G01N 1/14 210/791 |
| 2010/0326212 A1 | * | 12/2010 | Furey | ............... C12M 33/00 73/863.31 |
| 2012/0252110 A1 | | 10/2012 | Oura et al. | |

FOREIGN PATENT DOCUMENTS

| | | |
|---|---|---|
| JP | 2005-181336 A | 7/2005 |
| JP | 2012-200239 A | 10/2012 |

* cited by examiner

*Primary Examiner* — Jonathan M Hurst
(74) *Attorney, Agent, or Firm* — Pearne & Gordon LLP (57) ABSTRACT

A sterile sampling apparatus includes a first to seventh flow paths, a sampling section, a first and second pumps, and a first to sixth opening/closing mechanism. The sampling section is disposed in the seventh flow path. The first pump is disposed in the sixth flow path. The second pump is disposed in the seventh flow path. The second flow path includes a first opening/closing mechanism. The third flow path includes a second opening/closing mechanism. The fourth flow path includes a third opening/closing mechanism. The first flow path includes a fourth opening/closing mechanism. The sixth flow path includes a fifth opening/closing mechanism. The seventh flow path includes a sixth opening/closing mechanism. The rate of the second pump is higher than that of the first pump.

13 Claims, 7 Drawing Sheets

STERILE SAMPLING APPARATUS

CROSS-REFERENCE TO RELATED APPLICATIONS

The present application claims priority from Japanese Patent Application No. 2019-137233, filed Jul. 25, 2019, the entire content of which is incorporated herein by reference.

TECHNICAL FIELD

The presently disclosed subject matter relates a sterile sampling apparatus.

BACKGROUND ART

A culture apparatus for culturing cells that are to be used in regenerative medicine, or those that are to be used in production of bio-pharmaceuticals must be configured so that cultivation is enabled while maintaining a sterile environment for a long term. However, the characteristics and state of cells vary depending on culture conditions, the kind of the cell strain, and the like, with the result that cells having desired characteristics cannot be sometimes obtained. Therefore, the state of the cells and the culture environment must be checked at an arbitrary timing during a culture period. A precious sample is contained in a culture container, and therefore a culture medium containing cells, and the like must be carried out into a non-sterile space while maintaining a sterile environment.

In the case where a culture medium in an open cell incubator is to be sampled, conventionally, a sample is carried out into a non-sterile space through a pass box or the like that is disposed in adjacent to an incubator (for example, an isolator) which is maintained in a sterile environment. However, this system has a problem that the sampling operation requires much trouble and time.

As a countermeasure against the problem, a sampling system of the isolator type in which a plurality of cell incubators can be accommodated in an incubator that is maintained in a sterile environment has been proposed (for example, JP2012-200239). In the system, a one-way valve that, in order to maintain a sterile space, limits a flow of a culture solution to a direction from the inside of the sterile space to the outside is disposed, thereby maintaining the sterility of the interior of an isolator. The system requires an isolator system, and therefore is not suitable for a closed culture apparatus for culturing a large number of cells.

In the case of mass culture which produces bio-pharmaceuticals or the like, and in which a culture tank is used, a line for sampling is disposed in the culture tank, and a sample is recovered therefrom (for example, JP2005-181336). In this system, however, the sterility of a line that was once used in sampling cannot be ensured, and therefore lines the number of which is equal to the number of required samplings must be previously prepared.

SUMMARY

In production of cell products, bio-pharmaceuticals, or the like under a sterile environment, it is difficult to easily acquire samples for analysis in arbitrary amount and number for the sake of quality management. The presently disclosed subject matter provides a sterile sampling apparatus in which a sample for analysis can be easily acquired according to the purpose of the worker and the use, while maintaining the sterility of a sterile environment.

The inventors have intensively studied the problem, and developed a sterile sampling apparatus in which samples for analysis can be easily acquired according to the purpose of the worker and the use, while maintaining the sterility of a sterile environment. That is, the presently disclosed subject matter includes the following configurations.

(1) A sterile sampling apparatus including:
a first flow path configured to be connected to a first tank for accommodating a culture medium containing cells;
a second flow path configured to be connected to a second tank for accommodating a buffer solution;
a third flow path configured to communicate with ambient air:
a fourth flow path includes a first branch portion where the second flow path and the third flow path are configured to be joined together;
a fifth flow path includes a second branch portion where the first flow path and the fourth flow path are configured to be joined together;
a sixth flow path configured to branch off from a third branch portion which is downstream of the fifth flow path;
a seventh flow path configured to branch off from the third branch portion; and
a sampling section configured to be disposed in the seventh flow path,
wherein a first pump that sends a fluid in the sixth flow path is disposed in the sixth flow path,
wherein a second pump that sends a fluid in the seventh flow path is disposed in the seventh flow path,
wherein the second flow path includes a first opening/closing mechanism,
wherein the third flow path includes a second opening/closing mechanism,
wherein the fourth flow path includes a third opening/closing mechanism,
wherein the first flow path includes a fourth opening/closing mechanism,
wherein the sixth flow path includes a fifth opening/closing mechanism,
wherein the seventh flow path includes a sixth opening/closing mechanism, wherein the apparatus operates in a manner that, in a case where the first opening/closing mechanism is opened, the second opening/closing mechanism is closed, or, in a case where the second opening/closing mechanism is opened, the first opening/closing mechanism is closed,
wherein the apparatus operates in a manner that, in a case where the third opening/closing mechanism is opened, the fourth opening/closing mechanism is closed, or, in a case where the fourth opening/closing mechanism is opened, the third opening/closing mechanism is closed,
wherein the apparatus operates in a manner that, in a case where the fifth opening/closing mechanism is opened, the sixth opening/closing mechanism is closed, or, in a case where the sixth opening/closing mechanism is opened, the fifth opening/closing mechanism is closed, and
wherein a rate at which the fluid is sent by the second pump is higher than a rate at which the fluid is sent by the first pump.

(2) The sterile sampling apparatus according to (1), wherein the first flow path includes a one-way valve that limits movement of a fluid in the first flow path, to a direction from the first tank toward the second branch portion.

(3) The sterile sampling apparatus according to (1) or (2) wherein the first flow path further includes a first sterile connection connector.

(4) The sterile sampling apparatus according to any one of (1) to (3), wherein the first flow path further includes a sterilizing unit.

(5) The sterile sampling apparatus according to any one of (1) to (4), wherein the apparatus further includes a fluid identification sensor for identifying a fluid of the fifth flow path.

(6) The sterile sampling apparatus according to any one of (1) to (5), wherein the second flow path includes a second sterile connection connector.

(7) The sterile sampling apparatus according to any one of (1) to (6), wherein the second flow path which is upstream of the first opening/closing mechanism further includes an eighth flow path that branches off from the second flow path, and that communicates with a third tank for accommodating a buffer solution.

(8) The sterile sampling apparatus according to (7), wherein the eighth flow path includes a third sterile connection connector.

(9) The sterile sampling apparatus according to any one of (1) to (8), wherein the sampling section includes a sample recovering section in which a container for recovering a sample that is ejected from a sample ejecting portion of the sampling section is to be disposed.

(10) The sterile sampling apparatus according to any one of (1) to (9),
   wherein the sampling section is disposed in a middle of the seventh flow path,
   wherein the sampling section includes a sample storing portion for storing a predetermined amount of the sample,
   wherein an end of the seventh flow path communicates with the ambient air,
   wherein the second pump is disposed between the sampling section and the end of the seventh flow path,
   wherein a ninth flow path is disposed between the sample storing portion and the sample ejecting portion, and
   wherein the ninth flow path includes a seventh opening/closing mechanism.

(11) The sterile sampling apparatus according to (10), wherein the sampling section includes a level sensor that detects an amount of the sample which is stored in the sample storing portion.

(12) The sterile sampling apparatus according to any one of (1) to (8),
   wherein the sampling section is disposed in a middle of the seventh flow path,
   wherein the sampling section is a valve unit for storing a predetermined amount of the sample,
   wherein an end of the seventh flow path communicates with the ambient air, and
   wherein the second pump is disposed between the valve unit and the end of the seventh flow path.

(13) The sterile sampling apparatus according to any one of (1) to (12), wherein the sixth flow path includes a flow rate detecting unit.

According to the presently disclosed subject matter, when, during the entire period except recovery of the sample, the buffer solution is caused to be always flown through the flow paths through which the buffer solution and a gas commonly flow, the sterility of the environment of a culture tank can be maintained during a culture period. On the other hand, a sample for analysis can be recovered easily and quickly at any required time while maintaining the sterility of the environment of the culture tank.

DETAILED DESCRIPTION

Hereinafter, the presently disclosed subject matter will be described referring as necessary to the drawings by way of embodiments thereof. However, the following embodiments are not intended to limit the presently disclosed subject matter as defined in the appended claims, and all combinations of features described in the embodiments are not always essential to solving means of the presently disclosed subject matter.

In the specification, each of the terms such as "first," "second," and "third" is used for distinguishing one component from other components. For example, a first component may be referred to as a second component, and similarly the second component may be referred to as the first component without departing from the scope of the presently disclosed subject matter.

Figure 1A:
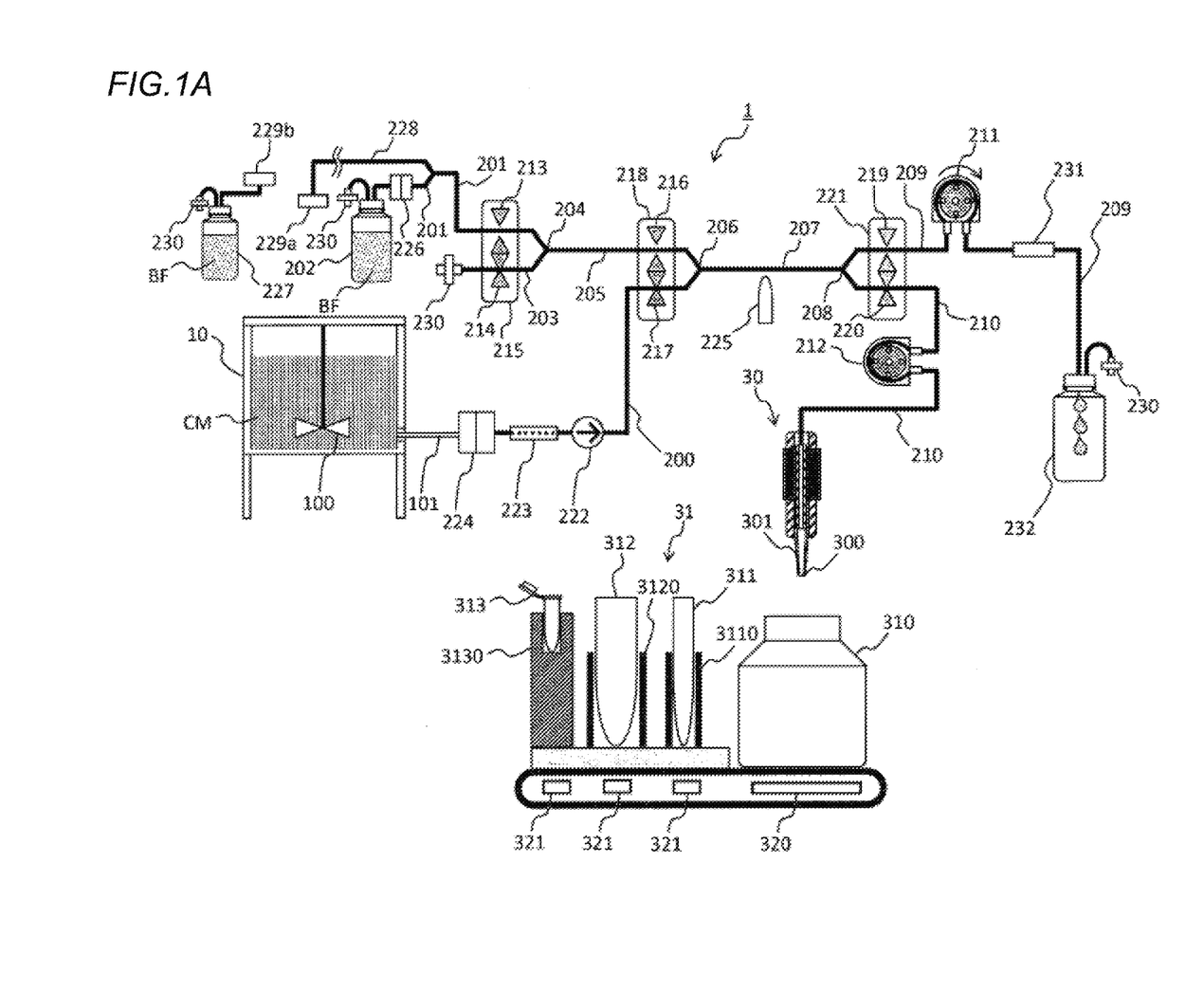
FIG. 1A is a schematic diagram of a sterile sampling apparatus of an embodiment.
Figure 1B:
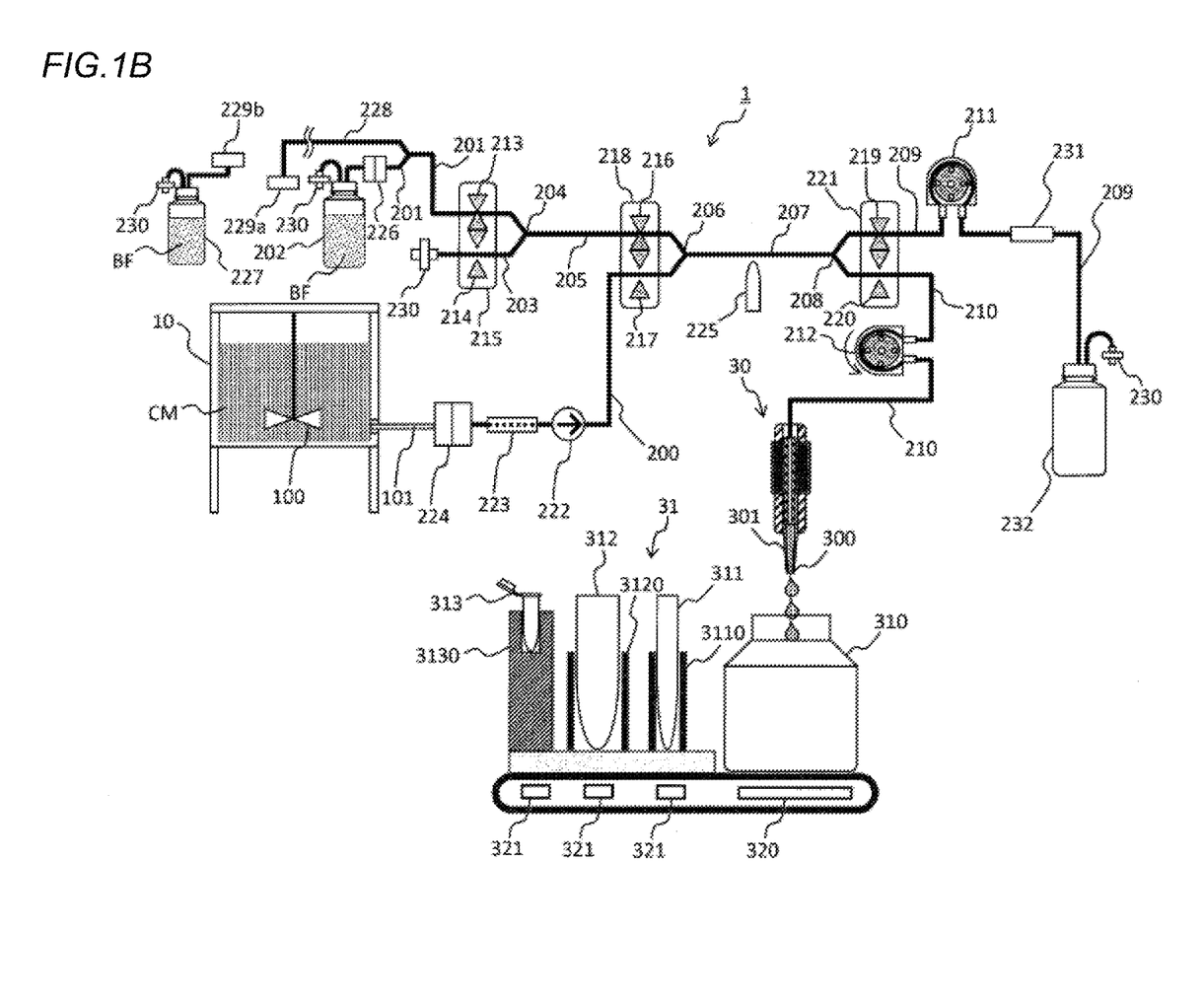
FIG. 1B is a schematic diagram of the sterile sampling apparatus of the embodiment.
Figure 1C:
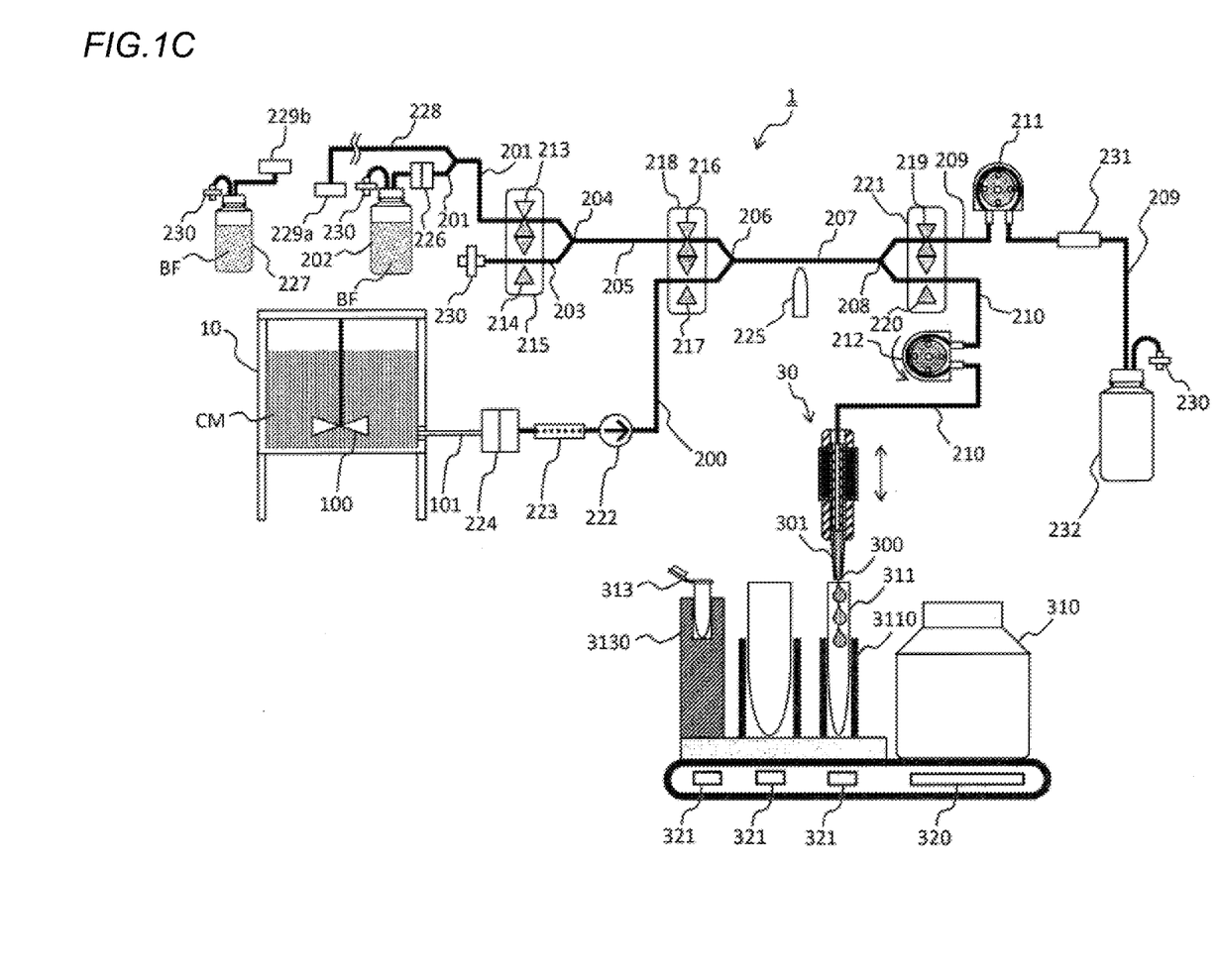
FIG. 1C is a schematic diagram of the sterile sampling apparatus of the embodiment.

<Sterile Sampling Apparatus (First Mode)>
FIGS. 1A to 1C are schematic diagrams of a sterile sampling apparatus 1 of an embodiment of the presently disclosed subject matter. In the embodiment, the sterile sampling apparatus 1 may include:
   a first flow path 200 that is to be connected to a first tank 10 for accommodating a culture medium containing cells;
   a second flow path 201 that is to be connected to a second tank 202 for accommodating a buffer solution;
   a third flow path 203 that communicates with the ambient air:
   a fourth flow path 205 that may include a first branch portion 204 where the second flow path 201 and the third flow path 203 join together;
   a fifth flow path 207 that may include a second branch portion 206 where the first flow path 200 and the fourth flow path 205 join together;
   a sixth flow path 209 that branches off from a third branch portion 208 which is downstream of the fifth flow path 207;
   a seventh flow path 210 that branches off from the third branch portion 208; and
   a sampling section 30 that is disposed in the seventh flow path 210, wherein
   the first flow path 200 may include a one-way valve 222 for limiting movement of a fluid in the first flow path 200, to a direction from the first tank 10 toward the second branch portion 206, a first pump 211 that sends a fluid in the sixth flow path 209 is disposed in the sixth flow path 209, a second pump 212 that sends a fluid in the seventh flow path 210 is disposed in the seventh flow path 210, the second flow path 201 may include a first opening/closing mechanism 213, the third flow path 203 may include a second opening/closing mechanism 214, the fourth flow path 205 may include a third opening/closing mechanism 216, the first flow path 200 may include a fourth opening/closing mechanism 217, the sixth flow path 209 may include a fifth opening/closing mechanism 219, the seventh flow path 210 may include a sixth opening/closing mechanism 220, the apparatus operates in a manner that, in a case where the first opening/closing mechanism 213 is opened, the second opening/closing mechanism 214 is closed, or, in a case where the second opening/closing 214 mechanism is opened, the first opening/closing mechanism 213 is closed, the apparatus operates in a manner that, in a case where the third opening/closing mechanism 216 is opened, the fourth opening/closing mechanism 217 is closed, or, in a case where the fourth opening/closing mechanism 217 is opened, the third opening/closing mechanism 216 is closed, the apparatus operates in a manner that, in a case where the fifth opening/closing mechanism 219 is opened, the sixth opening/closing mechanism 220 is closed, or, in a case where the sixth opening/closing mechanism 220 is opened, the fifth opening/closing mechanism 219 is closed, and a rate at which the fluid is sent by the second pump 212 is higher than a rate at which the fluid is sent by the first pump 211.

In the specification, "first tank 10 for accommodating a culture medium containing cells" means an arbitrary culture tank that is used in cell culture, and a box-type or flexible bag-type culture tank that is known can be used as the first tank 10. The capacity of the first tank 10 that is applied to the presently disclosed subject matter can be selected depending on the use, and is not particularly limited. The first tank 10 may be configured so that a first-tank discharge line 101 for feeding a sample to the sterile sampling apparatus of the presently disclosed subject matter is disposed in a part of the tank, that the first flow path 200 is sterilely connected to the tank, or that the tank communicates with the first flow path 200. Preferably, the first tank 10 is sterilely connected to the first flow path 200 through a sterile connection connector (in FIGS. 1A to 1C, a first sterile connection connector 224). The configuration in which the first tank 10 can be sterilely connected to the first flow path 200 through the first sterile connection connector 224 enables the first tank 10 and the sterile sampling apparatus 1 to be provided separately from each other, and combined together to be used at an arbitrary timing. When the first tank is sterilely connected to the first flow path 200 through the first sterile connection connector 224, it is not necessary to perform a sterilizing process between the first tank 10 and the first flow path 200 each time when the sterile sampling apparatus is to be used.

In the embodiment, the first flow path 200 includes the one-way valve 222 for limiting movement of the fluid in the first flow path 200, to the direction from the first tank 10 toward the second branch portion 206. This can prevent the fluid from reversely flowing toward the interior of the first tank 10, and reduce a risk of contaminating the interior of the first tank 10.

In the embodiment, the first flow path 200 may include a sterilizing unit 223. In the case where the sterilizing unit 223 is applied to the periphery of the first flow path 200, even when an abnormality occurs in a mechanism for sending a sample from the first tank 10 to a non-sterile space, bacteria are destroyed by the sterilizing unit 223, and therefore it is possible to prevent the interior of the first tank 10 from being contaminated.

In the specification, the sterilizing unit 223 means a unit that can eliminate living microorganisms, or that can reduce living microorganisms to a pre-designated level. For example, a unit using radiation rays (for example, gamma rays), electron beams, ultraviolet rays, or heat may be employed as the sterilizing unit 223. Gamma rays are emitted in the gamma decay of $^{60}$Co, $^{137}$Cs, or the like. The sterilizing unit 223 using gamma rays can damage biopolymers (particularly, DNA), and sterilize microorganisms. Also the sterilizing unit 223 using electron beams is a unit that can damage biological polymers (particularly, DNA), and sterilize microorganisms. In the case where the sterilizing unit 223 is a unit that applies heat to perform sterilization, for example, heating to 80° C. or higher, 90° C. or higher, 100° C. or higher, 110° C. or higher, 120° C. or higher, 130° C. or higher, 140° C. or higher, or 150° C. or higher can be applied to perform sterilization. In the case where the sterilizing unit 223 is a unit that applies ultraviolet rays to perform sterilization, ultraviolet rays can damage biopolymer (particularly, DNA) of microorganisms, and sterilize the microorganisms. The wavelength of ultraviolet rays that is useful in the sterilizing unit 223 in the presently disclosed subject matter is preferably a deep ultraviolet wavelength, or 200 to 350 nm, more preferably 230 to 330 nm, and further preferably 250 to 300 nm. Ultraviolet rays that are useful in the sterilizing unit 223 may be generated by using a known light source. For example, ultraviolet rays can be generated by using a light emitting diode (LED) that emits light at a deep ultraviolet wavelength. In the presently disclosed subject matter, preferably, the sterilizing unit 223 can be miniaturized, and easily attached and detached. For example, the sterilizing unit 223 using an LED that emits light at a deep ultraviolet wavelength is preferred.

In the case where the sterilizing unit 223 is applied, a part of the first flow path 200 to which the sterilizing unit 223 is applied is preferably formed by a material which does not prevent the sterilization effect from being exerted in the first flow path 200, and to which biological materials are hardly adsorbed. Such a material may be appropriately selected in accordance with the used sterilizing unit 223. In the case where the sterilizing unit 223 that uses gamma rays or electron beams is employed, for example, the first flow path 200 that does not disturb transmission of gamma rays or electron beams, and that is less deteriorated by gamma rays or electron beams may be used, and a tube that is conventionally used as a medical tube (e.g., a silicone rubber tube, a polyethylene tube, or a polyimide tube) may be employed. In the case where the sterilizing unit 223 is a unit that applies heat to perform sterilization, a silicone rubber tube, a metal-made tube, a polyimide tube, a fluorine resin tube, or the like may be used as the first flow path 200. In the case where the sterilizing unit 223 is a unit that uses ultraviolet rays, for example, a tube made of a material which does not disturb transmission of ultraviolet rays, and to which biological materials are hardly adsorbed, such as a fluorine resin tube (a PTFE tube, an FEP tube, a THV tube, a PFA tube, an ETFE tube, or a PVDF tube) may be employed. Preferably, an FEP tube may be employed.

The sterile sampling apparatus 1 of the presently disclosed subject matter may include the second flow path 201 that is to be connected to the second tank 202 for accommodating the buffer solution. As the buffer solution that is injected into the second tank 202, a solution may be used which has characteristics that suppresses a pH variation to a minimum level in order to prevent the properties of materials contained in the sample (for example, the culture medium containing cells in the first tank 10) to be recovered, from being changed. For example, useful are a liquid culture medium (such as DMEM, RPM1-1640, or the like) that is used for culture of cells, a phosphate buffer solution, a Tris buffer solution, a HEPES buffer solution, a HEPPS buffer solution, a citrate buffer solution, a boric acid buffer solution, or the like. The kind of the buffer solution may be appropriately selected in accordance with the kind and purpose of the sample to be recovered. In place of the buffer solution, water or a physiological saline solution may be used.

As the second tank 202, a tank that is previously connected sterilely to the second flow path 201 may be provided. Alternatively, a tank that is connected sterilely to the second flow path through a sterile connection connector (in FIGS. 1A to 1C, a second sterile connection connector 226) may be provided. In the case where the second flow path 201 has the second sterile connection connector 226, the second tank 202 and the sterile sampling apparatus 1 can be provided separately from each other, and combined together to be used at an arbitrary timing.

In another mode, the second flow path 201 that is upstream of the first opening/closing mechanism 213 (described later) may include an eighth flow path 228 that branches off from the second flow path, and that communicates with a third tank 227 for accommodating a buffer solution. According to the configuration, in the case where all of the entire buffer solution or the like in the second tank 202 is discharged, the third tank 227 containing the buffer solution can be additionally connected to the sterile sampling apparatus 1. Preferably, the eighth flow path 228 may include a sterile connection connector (in FIGS. 1A to 1C, a third sterile connection connector (male type) 229a). This enables the eighth flow path to be connected sterilely and at an arbitrary timing to the third tank 227 having a third sterile connection connector (female type) 229b. In the second flow path 201, in this case, the place where the eighth flow path 228 branches off from the second flow path 201 may be shut off by a device (such as forceps or a pinch valve) that can sterilely perform a shut-off operation. In a further mode, the second flow path 201 may have a configuration where it includes two or more branching flow paths, and it is connected to tanks that accommodate two or more additional buffer solutions, respectively.

In each of the sterile connection connectors (for example, the first sterile connection connector 224, the second sterile connection connector 226, and the third sterile connection connector 229) that can be used in the presently disclosed subject matter, a male type sterile connection connector (for example, the third sterile connection connector (male type) 229a in FIGS. 1A to 1C) and a female-type sterile connection connector (for example, the third sterile connection connector (female type) 229b in FIGS. 1A to 1C) are combined with each other, and membrane strips (not illustrated) that hermetically close openings of the sterile connection connectors, respectively are pulled and peeled off, whereby the connectors can be sterilely coupled to each other. As the sterile connection connectors, commercially available ones can be used. For example, the connectors are available from Pall Corporation (USA), Sartorius AG (Germany), Colder Products Company (USA), or the like. The male-type and female-type sterile connection connectors may be exchangedly used.

The third flow path 203 that communicates with the ambient air joins with the second flow path 201 in the first branch portion 204, and communicates with the fourth flow path 205. The end of the third flow path 203 may include a ventilation filter 230 that prevents the interior of the flow path from being contaminated, and that does not disturb suction of a gas into the flow path.

The first flow path 200 and the fourth flow path 205 join together in the second branch portion 206, and communicate with the fifth flow path 207. Namely, the culture medium in the first tank 10, the buffer solution in the second tank 202 (or the third tank 227), and a gas commonly pass through the fifth flow path 207.

In the third branch portion 208 that is downstream of the fifth flow path 207, the fifth flow path branches into the sixth flow path 209 and the seventh flow path 210. The end of the sixth flow path 209 is connectable to a first waste liquid bottle 232 having the ventilation filter 230. The sampling section 30 is disposed in the seventh flow path 210. The sampling section 30 ejects a collected sample from a sample ejecting portion 300. In the embodiment, for example, the sample ejecting portion 300 may be a disposable tip 301 that fluidly communicates with the seventh flow path 210, and that is to be attached to a pipette. In the embodiment, the sampling section 30 may be configured so that it can be moved to arbitrary coordinates by a mechanism that is movable in upward/downward, forward/rearward, and/or rightward/leftward directions.

In the embodiment, the sterile sampling apparatus 1 may include a sample recovering section 31 in which a container for recovering a sample that is ejected from the sample ejecting portion 300 of the sampling section 30 is to be disposed. For example, the sample recovering section 31 may include a second waste liquid bottle 310. The second waste liquid bottle 310 recovers waste liquid that is discharged after the flow path in the sampling section 30 is washed with a buffer solution. In the sample recovering section 31 in which the second waste liquid bottle 310 is disposed, for example, a first fluid detecting unit 320 is disposed, and the amount of the waste liquid that is discharged into the second waste liquid bottle 310 can be monitored. The first fluid detecting unit 320 (and a second fluid detecting unit 321 that will be described later) may be any kind of unit that can monitor the amount of the waste liquid that is discharged into the second waste liquid bottle 310, and may be, for example, a weight sensor, a level sensor, a CCD camera, or the like.

In the embodiment, arbitrary sample recovery containers such as a 15 mL centrifuge pipe 311, a 50 mL centrifuge pipe 312, and/or a 1.5 mL centrifuge tube 313 can be disposed in the sample recovering section 31. In order to dispose an arbitrary sample recovery container, for example, a 15 mL centrifuge pipe holder 3110, a 50 mL centrifuge pipe holder 3120, and/or a 1.5 mL centrifuge tube holder 3130 are disposed in the sample recovering section 31. According to the configuration, the 15 mL centrifuge pipe 311, 50 mL centrifuge pipe 312, and/or 1.5 mL centrifuge tube 313 that are commercially available can be disposed in the sample recovering section 31. In the sample recovering section 31 in which the 15 mL centrifuge pipe 311, the 50 mL centrifuge pipe 312, and/or the 1.5 mL centrifuge tube 313 are disposed, for example, the second fluid detecting unit 321 is disposed, and the amounts of samples that are discharged into the 15 mL centrifuge pipe 311, the 50 mL centrifuge pipe 312, and/or the 1.5 mL centrifuge tube 313 can be monitored. In the embodiment, the sample recovering section 31 may be configured so that it can be moved to arbitrary coordinates by a mechanism that is movable in upward/downward, forward/rearward, and/or rightward/leftward directions. According to the configuration, a sample that is discharged from the sample ejecting portion 300 can be surely recovered. Sample recovery containers that can be disposed in the sample recovering section 31 are not limited to those described above, and may be appropriately selected in accordance with the use.

The first pump 211 that sends the fluid in the sixth flow path 209 is disposed in the sixth flow path 209, and the second pump 212 that sends the fluid in the seventh flow path 210 is disposed in the seventh flow path 210. A sample, the buffer solution, or a gas can be sent to the sampling section 30 by driving the first pump 211. The first pump 211 and the second pump 212 may be a tube pump (peristaltic pump), or a piezoelectric pump, and any type of pump can be used as far as it can send a fluid.

The first pump 211 is mainly used for causing the buffer solution contained in the second tank 202 (or the third tank 227 or the like) to continue to flow through the flow paths, thereby preventing the first flow path 200 from being contaminated with bacteria and the like. From the viewpoint of saving the amount of the used buffer solution, therefore, it is preferred that a pump the rate of which is as low as possible is used as the first pump 211. On the other hand, the second pump 212 is mainly used for sending the sample in the first tank 10 to the sampling section 30, and preferably the rate of the pump is at a level at which the characteristics of the sample is not impaired. The flow rates of the first and second pumps 211 and 212 are appropriately adjusted in accordance with the diameters of the flow paths, the amount of the sample to be handled, that of the culture medium in the first tank 10, that of the buffer solution in the second tank 202 (or the third tank 227 or the like), and so on, and therefore are not specifically limited. In the embodiment, however, it is preferable that the rate at which the fluid is sent by the second pump 212 is higher than that at which the fluid is sent by the first pump 211.

The second flow path 201 has the first opening/closing mechanism 213, and the third flow path 203 has the second opening/closing mechanism 214. The apparatus operates in a manner that, in the case where the first opening/closing mechanism 213 is opened, the second opening/closing mechanism 214 is closed, or, in the case where the second opening/closing 214 mechanism is opened, the first opening/closing mechanism 213 is closed. This prevents the fluids that are contained respectively in the second and third flow paths 201 and 203, from being simultaneously sent into the fourth flow path 205. In the embodiment, the first opening/closing mechanism 213 and the second opening/closing mechanism 214 are alternately opened and closed by a first opening/closing switching device 215.

The fourth flow path 205 has the third opening/closing mechanism 216, and the first flow path 200 has the fourth opening/closing mechanism 217. The apparatus operates in a manner that, in the case where the third opening/closing mechanism 216 is opened, the fourth opening/closing mechanism 217 is closed, or, in the case where the fourth opening/closing mechanism 217 is opened, the third opening/closing mechanism 216 is closed. This prevents the fluids that are contained respectively in the fourth and first flow paths 205 and 200, from being simultaneously sent into the fifth flow path 207. In the embodiment, the third opening/closing mechanism 216 and the fourth opening/closing mechanism 217 are alternately opened and closed by a second opening/closing switching device 218.

The sixth flow path 209 has the fifth opening/closing mechanism 219, and the seventh flow path 210 has the sixth opening/closing mechanism 220. The apparatus operates in a manner that, in the case where the fifth opening/closing mechanism 219 is opened, the sixth opening/closing mechanism 220 is closed, or, in the case where the sixth opening/closing mechanism 220 is opened, the fifth opening/closing mechanism 219 is closed. This enables the fluid to be selectively sent into the desired one of the sixth and seventh flow paths 209 and 210. In the embodiment, the fifth opening/closing mechanism 219 and the sixth opening/closing mechanism 220 are alternately opened and closed by a third opening/closing switching device 221.

The first to sixth opening/closing mechanisms (and a seventh opening/closing mechanism that will be described later) are requested to be mechanisms for opening and closing the respective flow paths, and configured by, for example, opening/closing valves, or preferably pinch valves. In the case where pinch valves are used, the flow of the fluid in the respective flow paths can be blocked by pinching the flow path. In the embodiment, in the case where the first to sixth opening/closing mechanisms (and the seventh opening/closing mechanism that will be described later) are configured by pinch valves, the flow paths (the first to ninth flow paths) are preferably configured by tubes that can be sterilized, and that are flexible, respectively, and for example medical tubes (e.g., silicone rubber tubes, polyethylene tubes, polyimide tubes, or fluorine resin tubes) may be employed.

In the embodiment, the sterile sampling apparatus 1 may include a fluid identification sensor 225 for identifying the fluid in the fifth flow path 207. The fluid identification sensor 225 can identify the kind of the fluid flowing through the fifth flow path 207, such as a culture medium containing a sample, a buffer solution, or a gas (for example, the air). A known sensor such as an optical sensor or a proximity sensor can be used as the fluid identification sensor 225. In the case where an optical sensor is used, for example, a light beam of a predetermined wavelength is orthogonally impinged on the fifth flow path 207, and a reflected or transmitted light beam is detected, whereby the kind of the fluid can be identified. In the case where the kind of the fluid flowing through the fifth flow path 207 is changed (for example, in the case where a buffer solution is changed to the air), particularly, a detected signal is largely varied, and therefore it is possible to identify that the kind of the fluid is changed.

In the embodiment, the sixth flow path 209 may include a flow rate detecting unit 231 (for example, a flow meter). Because of the flow rate detecting unit 231, the flow rate of the fluid (for example, a buffer solution) passing through the sixth flow path 209 can be monitored, it is possible to confirm that the flow of the fluid (particularly, the buffer solution or the like) is surely maintained in the flow paths (particularly, the fifth flow path 207), and the interior of the first tank 10 can be prevented from being contaminated.

<Sterile Sampling Apparatus (Second Mode)>

Figure 2:
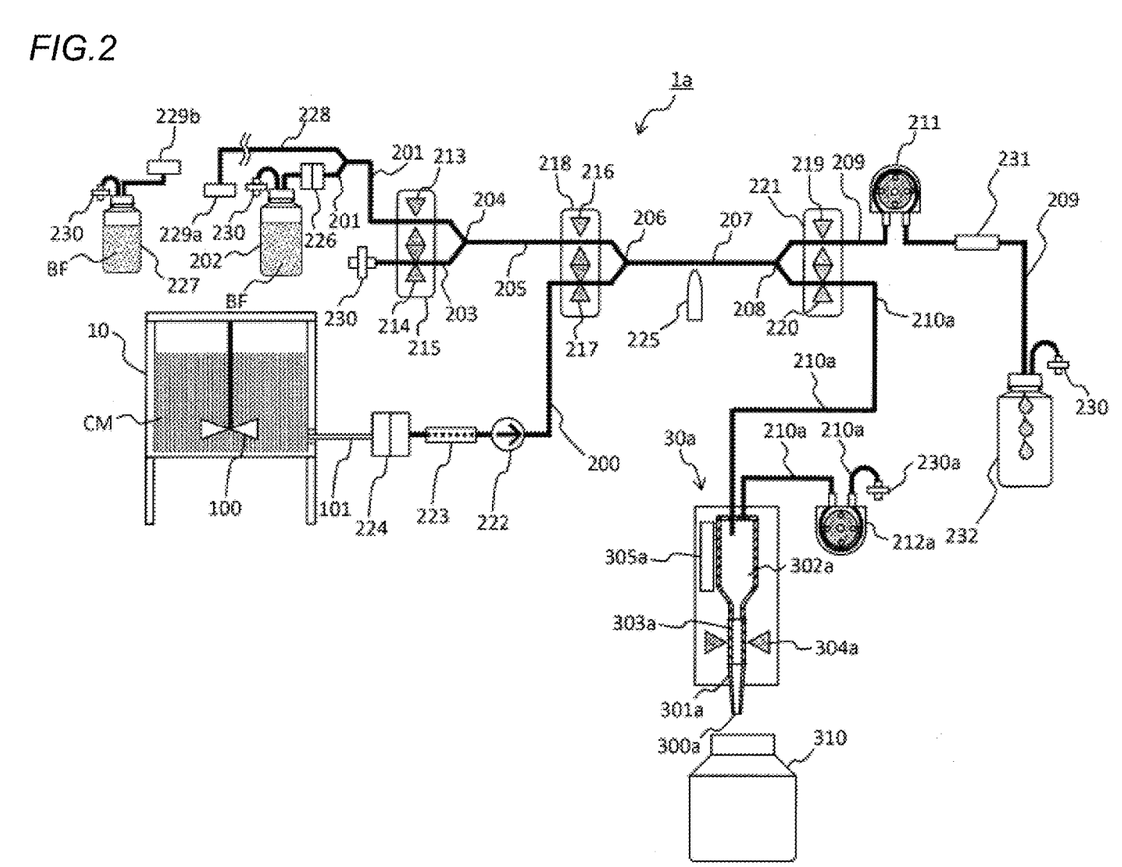
FIG. 2 is a schematic diagram of a sterile sampling apparatus of another embodiment.
Figure 3A:
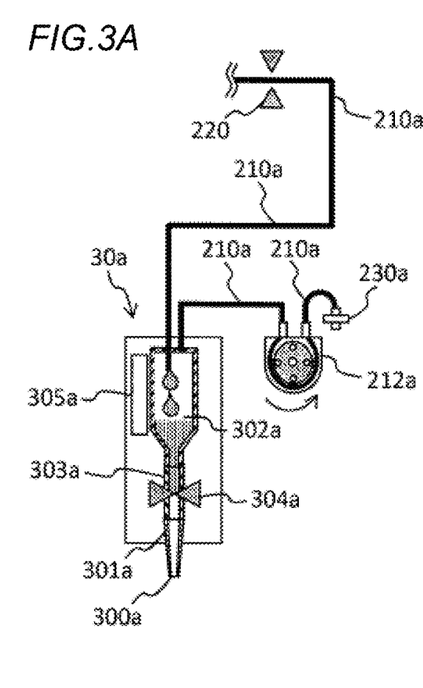
FIGS. 3A and 3B illustrate an operation of a sampling section in the sterile sampling apparatus of FIG. 2.
Figure 3B:
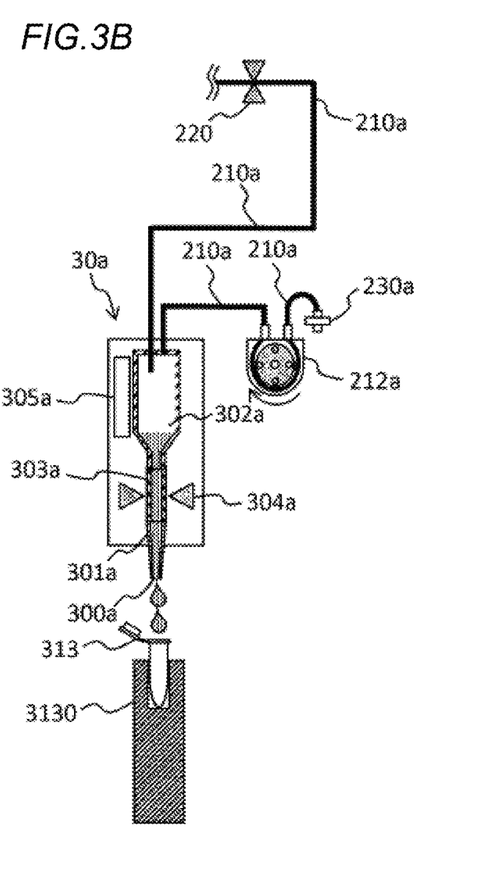

FIG. 2 is a schematic diagram of a sterile sampling apparatus 1a of another embodiment of the presently disclosed subject matter, and FIGS. 3A and 3B illustrate the operation of a sampling section 30a. With respect to members that are common to the sterile sampling apparatus 1, their description will be omitted. In the embodiment, the sampling section 30a of the sterile sampling apparatus 1a is disposed in the middle of a seventh flow path 210a, and the sterile sampling apparatus 1a is configured so that the sampling section 30a may include a sample storing portion 302a for storing a predetermined amount of the sample, the end of the seventh flow path 210a communicates with the ambient air, a second pump 212a is disposed between the sampling section 30a and the end of the seventh flow path 210a, a ninth flow path 303a is disposed between the sample storing portion 302a and a sample ejecting portion 300a, and the ninth flow path 303a may include a seventh opening/closing mechanism 304a.

In the embodiment, the second pump 212a is disposed between the sampling section 30a and the end of the seventh flow path 210a, i.e., downstream of the sampling section 30a. Therefore, for example, a sample containing cells can be recovered without passing through a flow path including a pump, and physical stress applied to the cells can be reduced. Preferably, the end of the seventh flow path 210a may include a ventilation filter 230a.

The sampling section 30a includes the sample storing section 302a that stores a predetermined amount of a sample. The capacity of the sample storing section 302a may be appropriately selected depending on the use, the object, and the like, and is not particularly limited.

The ninth flow path 303a is disposed between the sample storing portion 302a and the sample ejecting portion 300a. The ninth flow path 303a includes the seventh opening/closing mechanism 304a. When the seventh opening/closing mechanism 304a is closed, and the second pump 212a is driven in the direction indicated in FIG. 3A, the interior of the sample storing section 302a is set to a negative pressure, and the sample can be stored in the sample storing section 302a (see FIG. 3A).

When the seventh opening/closing mechanism 304a is opened, the sixth opening/closing mechanism 220 is closed, and the second pump 212a is driven in the direction indicated in FIG. 3B, the interior of the sample storing section 302a is set to a positive pressure, and the sample can be discharged from the sample ejecting portion 300a (see FIG. 3B).

In the embodiment, the sampling section 30a may include a level sensor 305a that detects the amount of the sample which is stored in the sample storing portion 302a. The amount of the sample which is stored in the sample storing portion 302a can be detected by the level sensor 305a, and it is possible to determine whether a desired amount of the sample is stored in the sample storing portion 302a or not.

<Sterile Sampling Apparatus (Third Mode)>

Figure 4:
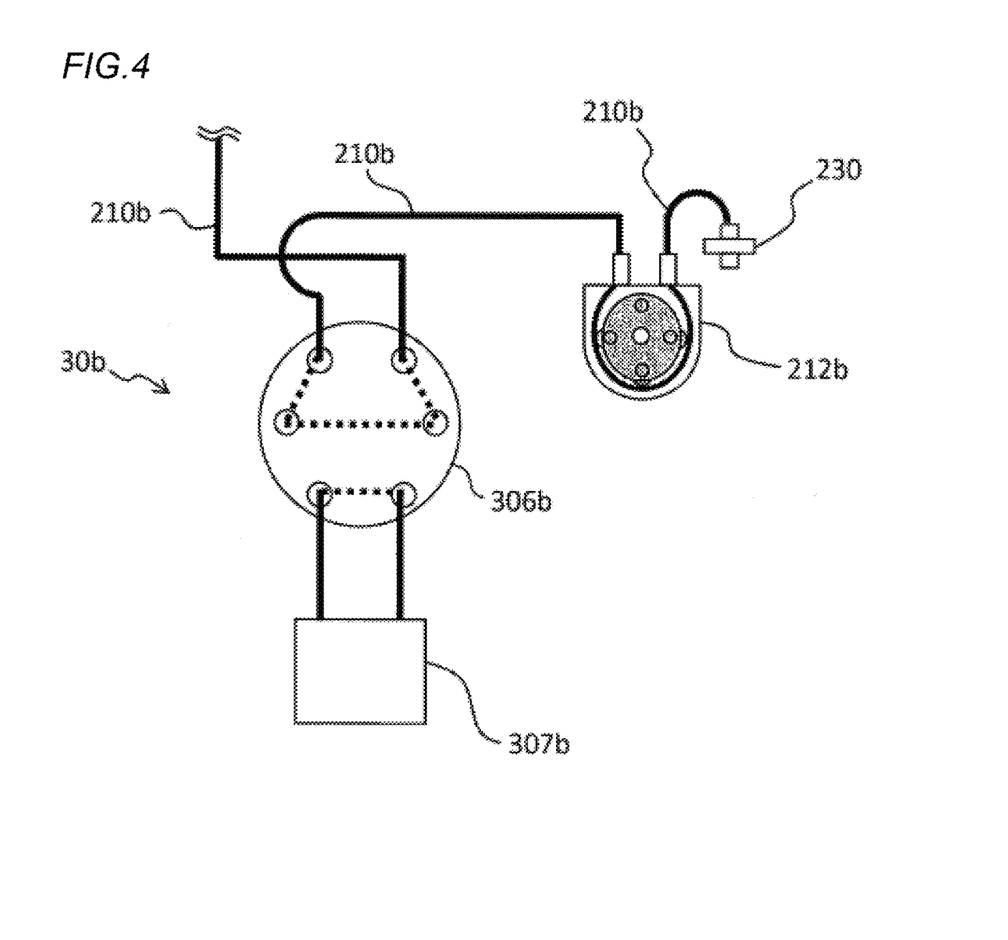
FIG. 4 is a schematic diagram of a sampling section of a sterile sampling apparatus of a further embodiment.

FIG. 4 is a schematic diagram of a sampling section 30b of a sterile sampling apparatus of a further embodiment of the presently disclosed subject matter.

In the embodiment, the sampling section 30b is disposed in the middle of a seventh flow path 210b, and the sterile sampling apparatus is configured so that the sampling section 30b is a valve unit 306b for storing a predetermined amount of the sample, the end of the seventh flow path 210b communicates with the ambient air, and a second pump 212b is disposed between the valve unit 306b and the end of the seventh flow path 210b.

As the valve unit 306b, a known valve unit that can recovery a sample while switching a flow path may be used. Furthermore, a desired component of the sample can be measured by an instrument 307b connected to the valve unit 306b.

In the embodiments of the presently disclosed subject matter, the sterile sampling apparatus 1, 1a may include: a controller (for example, a CPU unit) that comminutes with the above-described components to control them; an inputting section (for example, a keyboard, a mouse, and/or a touch panel); and an outputting section (for example, a monitor device or a touch panel) (these sections are not illustrated).

<Method of Recovering Sample by Using Sterile Sampling Apparatus>

Figure 5:
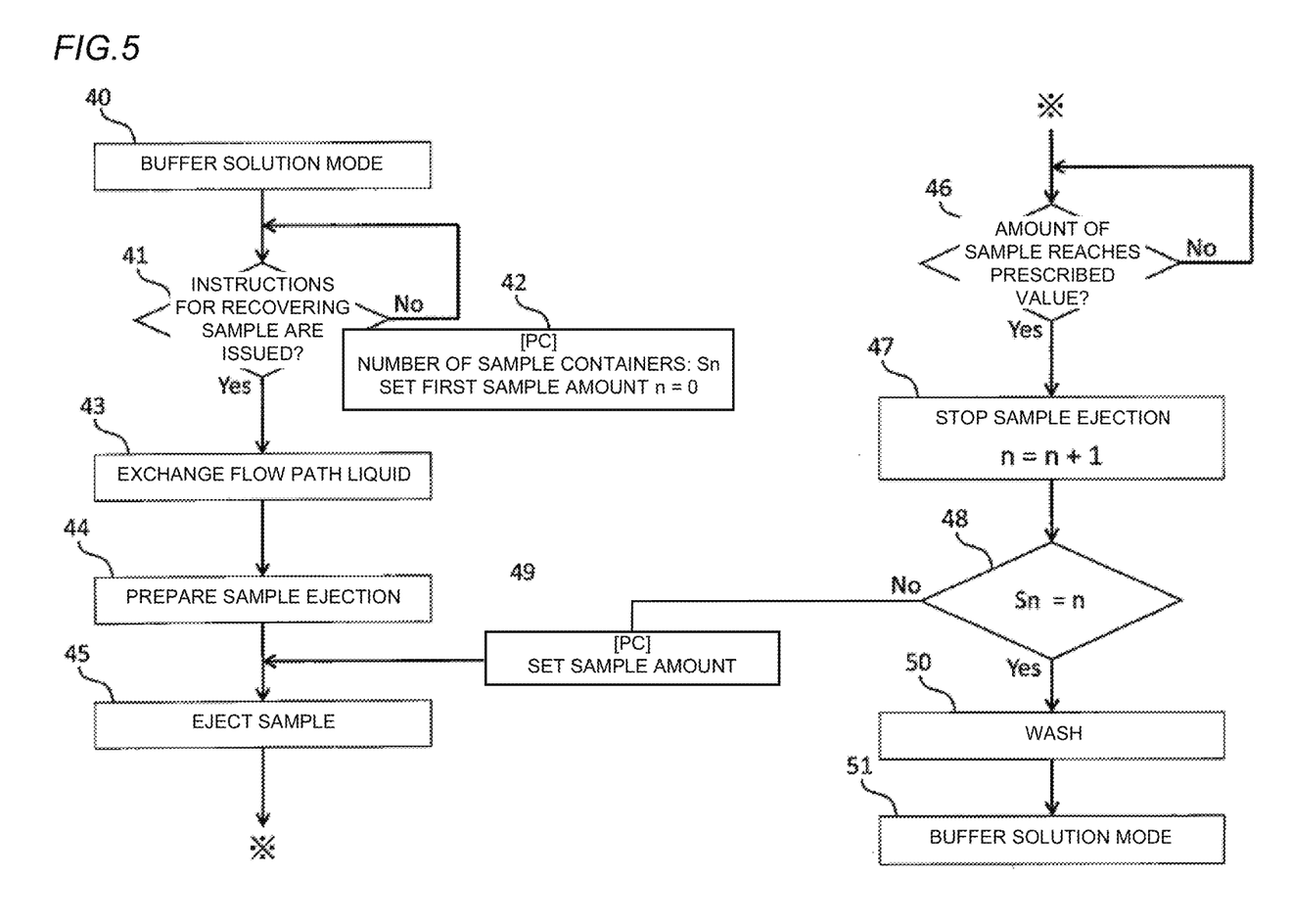
FIG. 5 is a flowchart illustrating an operation of a sampling section in the sterile sampling apparatus of the embodiment.

FIGS. 1A to 1C are diagrams illustrating the operation of the sterile sampling apparatus 1 of the embodiment, and FIG. 5 is a flowchart illustrating the operation of the sterile sampling apparatus 1.

A method of recovering the sample by using the sterile sampling apparatus 1 will be described with reference to the drawing and the following table.

TABLE 1

| | | Operating member (abbreviation) Reference numeral | | | | | | | | | |
|---|---|---|---|---|---|---|---|---|---|---|---|
| | Step | Pump-1 211 | Pump-2 212 | Valve-1 215 | Valve-2 218 | Valve-3 221 | Sensor-1 225 | Sensor-2 231 | Sensor-3 320 | Sensor-4 321 | Reference FIG. |
| #1 | Buffer solution mode | ON | OFF | Upper | Upper | Upper | L | Y | — | — | FIG. 1A |
| #2 | Filling of air | ON | OFF | Lower | Upper | Upper | L | Y | — | — | |
| #3 | Detection air | ON | OFF | Lower | Upper | Upper | A | Y | — | — | |
| #4 | Exchange of flow path liquid | OFF | ON | Lower | Lower | Lower | L | N | Y→N | — | FIG. 1B |
| #5 | Recovery of sample | OFF | ON | Lower | Lower | Lower | L | N | — | Y | FIG. 1C |
| #6 | Wash of sampling section -1 | OFF | ON | Upper | Upper | Lower | L | N | Y→N | — | |
| #7 | Wash of sampling section -2 | OFF | ON | Lower | Upper | Lower | A | N | Y→N | — | |
| #8 | Buffer solution mode | ON | OFF | Upper | Upper | Upper | L | Y | — | — | FIG. 1A |

In Table 1, "Operating member" means the members of the sterile sampling apparatus 1 that are caused to operate in the respective steps. The members are abbreviated in Table 1. The reference numerals of the members correspond to the numerals that are listed below "Operating member," and coincide with the reference numerals which are described above, respectively.

In Table 1, "Pump-1" and "Pump-2" indicate "first pump 211" and "second pump 212," respectively. "ON" indicates that the corresponding pump is operating, and "OFF" indicates that the corresponding pump is not operating.

In Table 1, "Valve-1," "Valve-2," and "Valve-3" correspond to "first opening/closing switching device 215," "second opening/closing switching device 218," and "third opening/closing switching device 221," respectively. The terms "Upper" and "Lower" described in Table 1 indicate the position of the opened opening/closing mechanism in the piping diagrams of FIGS. 1A to 1C. When "Valve-1" is "Upper," for example, it indicates the state where the first opening/closing mechanism 213 is "opened," and the second opening/closing mechanism 214 is "closed."

In Table 1, "Sensor-1," "Sensor-2," "Sensor-3," and "Sensor-4" correspond to "fluid identification sensor 225," "flow rate detecting unit 231," "first fluid detecting unit 320," and "second fluid detecting unit 321," respectively.

"Sensor-1" determines whether the fluid is a buffer solution, the air, or a sample. In Table 1, "L" indicates that "liquid" is detected, and "A" indicates that "air" is detected.

"Sensor-2" measures the flow rate of the liquid flowing through the sixth flow path 209. In Table 1, "Y" indicates that the flow of the liquid is detected, and "N" indicates that the flow of the liquid is not detected.

Sensor-3 detects the amount of the sample ejected into the second waste liquid bottle 310. In Table 1, "Y" indicates that the amount is increased by the buffer solution or sample that is ejected from the sample ejecting portion 300. "Y→N" indicates that the amount is increased by the buffer solution or sample that is ejected from the sample ejecting portion 300, and then the stop of the increase of the amount is detected.

Sensor-4 detects the amount of the sample ejected into the sample recovery container (for example, the 15 mL centrifuge pipe 311, the 50 mL centrifuge pipe 312, or the 1.5 mL centrifuge tube 313). In Table 1, "Y" indicates that the amount of the buffer solution or sample that is ejected from the sample ejecting portion 300 reaches a predetermined amount.

Basic steps will be described with dividing them into Steps 1 to 8 indicated in Table 1.

Step 1. Buffer Solution Mode:

The buffer solution is continuously supplied to the fifth flow path 207, and then discharged into the first waste liquid bottle 232 through the sixth flow path 209 (see FIG. 1A). A contaminant (such as bacteria) can be prevented from entering through the first flow path 200 that communicates with the first tank 10 in which culture is performed for a long term, and the interior of the first tank 10 can be prevented from being contaminated.

Step 2. Filling of Air:

The air is introduced from the third flow path 203 that communicates with the ambient air through the ventilation filter 230.

Step 3. Detection of Air:

The air that is introduced in Step 2 is detected by Sensor-1.

Step 4. Exchange of Flow Path Liquid:

The second pump 212 is operated, the sample in the first tank 10 is introduced into the first flow path 200, the fifth flow path 207, and the seventh flow path 210 by the negative pressure, and the sample is sucked until the sample is ejected into the second waste liquid bottle 310. This causes the buffer solution that remains in the flow paths, to be exchanged with a solution constituting the sample. The first fluid detecting unit 320 senses the increase of the amount of the sample, and therefore it is possible to, after a predetermined amount of the sample is ejected from the sample ejecting portion 300, sense a stop of the ejection (see FIG. 1B).

Step 5. Recovery of Sample:

After Step 4, the second pump 212 is once stopped, the sampling section 30 or the sample recovering section 31 is moved, and then the sample ejecting portion 300 is inserted into a desired one of the sample recovery containers to prepare the sample ejection. During the movement of the sampling section 30 or the sample recovering section 31, the first pump is operated, and the fifth opening/closing mechanism 219 is opened. When the movement of the sampling section 30 or the sample recovering section 31 is then ended, the first pump is stopped, the sixth opening/closing mechanism 220 is opened, and the second pump 212 is operated, thereby recovering the sample into the sample recovery container. At the timing when the sample amount detected by the second fluid detecting unit 321 exceeds a predetermined threshold, the second pump 212 is stopped (FIG. 1C).

Step 6. Washing of Sampling Section-1:

The sample ejecting portion 300 is relatively moved above the second waste liquid bottle 310 by moving the sampling section 30 or the sample recovering section 31. During the movement of the sampling section 30 or the sample recovering section 31, the first pump is operated, and the fifth opening/closing mechanism 219 is opened. When the movement of the sampling section 30 or the sample recovering section 31 is then ended, the first pump is stopped, the sixth opening/closing mechanism 220 is opened, Valve-1 and Valve-2 are switched, and the second pump 212 is operated, whereby the buffer solution is introduced into the second flow path 201, the fifth flow path 207, and the seventh flow path 210, and the buffer solution is discharged into the second waste liquid bottle 310 until the discharge amount reaches the predetermined amount.

Step 7. Washing of Sampling Section-2:

Valve-1 is switched, and the second pump 212 is operated, whereby the air is introduced from the third flow path 203, and the air is discharged from the sample ejecting portion 300 through the fifth flow path 207 and the seventh flow path 210. The first fluid detecting unit 320 senses a stop of the increase of the weight, thereby enabling the situation where the buffer solution is discharged from all of the fifth flow path 207, the seventh flow path 210, and the sampling section 30, to be sensed. Thereafter, the disposable tip 301 is replaced with a new disposable tip 301.

Step 8. Buffer Solution Mode:

A step that is basically same as or similar to Step 1 above is executed.

When Steps 1 to 8 are executed, the buffer solution is caused to, during the entire period except recovery of the sample, be always flown through the flow paths for recovering the sample, whereby the sterility of the environment of the culture tank can be maintained during the culture period. On the other hand, a sample for analysis can be recovered easily and quickly at a required time while maintaining the sterility of the environment of the culture tank. In arbitrary ones of Steps 1 to 8 above may be repeated. When Steps 6 and 7 are repeated a desired number of times, for example, the sample remaining in the fifth flow path 207, the seventh flow path 210, and the sampling section 30 can be sufficiently washed away.

Steps 1 to 8 above may be realized as a sterile sampling apparatus that is program controlled by the above-described controller, and that can automatically perform sampling. The sterile sampling apparatus of the presently disclosed subject matter may be operated in accordance with, for example, the flowchart illustrated in FIG. 5.

In the case where instructions for recovering the sample (41 in FIG. 5) are issued in the buffer solution mode (40 in FIG. 5, Step 1), for example, the flow path liquid is exchanged (43 in FIG. 5, Steps 2 to 4 above). The recovery amount of the sample, and the sample number (the number of sample containers) are previously input through the inputting section (42 in FIG. 5). The sample ejecting portion 300 is inserted into a desired one of the sample recovery containers to prepare the sample ejection (44 in FIG. 5). The sample is ejected into the sample recovery container (45 in FIG. 5, Step 5), and, when the recovered amount of the sample reaches a prescribed value, the ejection of the sample is stopped (46 and 47 in FIG. 5, Step 5). If the recovered sample number does not reach the preset number of sample containers (48 in FIG. 5), the sample is further ejected into the sample recovery container in accordance with the sample recovery amount that is previously input through the inputting section (49 in FIG. 5). If the recovered sample number reaches the preset number of sample containers (48 in FIG. 5), the washing step (Steps 6 and 7) is executed (50 in FIG. 5). When the washing step is ended, the process returns to the buffer solution mode (51 in FIG. 5, Step 8).

Although the presently disclosed subject matter has been described by way of the embodiments, the technical scope of the presently disclosed subject matter is not restricted to the scope of the description of the embodiments. It is obvious to those skilled in the art that various changes or improvements can be made on the embodiments.

What is claimed is:

1. A sterile sampling apparatus comprising:
   a first flow path configured to be connected to a first tank for accommodating a culture medium containing cells;
   a second flow path configured to be connected to a second tank for accommodating a buffer solution;
   a third flow path configured to communicate with ambient air;
   a fourth flow path includes a first branch portion where the second flow path and the third flow path are configured to be joined together;
   a fifth flow path includes a second branch portion where the first flow path and the fourth flow path are configured to be joined together;
   a sixth flow path configured to branch off from a third branch portion which is downstream of the fifth flow path;
   a seventh flow path configured to branch off from the third branch portion; and
   a sampling section configured to be disposed in the seventh flow path,
   wherein a first pump that sends a fluid in the sixth flow path is disposed in the sixth flow path,
   wherein a second pump that sends a fluid in the seventh flow path is disposed in the seventh flow path,
   wherein the second flow path includes a first opening/closing mechanism,
   wherein the third flow path includes a second opening/closing mechanism,
   wherein the fourth flow path includes a third opening/closing mechanism,
   wherein the first flow path includes a fourth opening/closing mechanism,
   wherein the sixth flow path includes a fifth opening/closing mechanism,
   wherein the seventh flow path includes a sixth opening/closing mechanism,
   wherein the apparatus operates in a manner that, in a case where the first opening/closing mechanism is opened, the second opening/closing mechanism is closed, or, in a case where the second opening/closing mechanism is opened, the first opening/closing mechanism is closed,
   wherein the apparatus operates in a manner that, in a case where the third opening/closing mechanism is opened, the fourth opening/closing mechanism is closed, or, in a case where the fourth opening/closing mechanism is opened, the third opening/closing mechanism is closed,
   wherein the apparatus operates in a manner that, in a case where the fifth opening/closing mechanism is opened, the sixth opening/closing mechanism is closed, or, in a case where the sixth opening/closing mechanism is opened, the fifth opening/closing mechanism is closed, and
   wherein a rate at which the fluid is sent by the second pump is higher than a rate at which the fluid is sent by the first pump.

2. The sterile sampling apparatus according to claim 1, wherein the first flow path includes a one-way valve that limits movement of a fluid in the first flow path, to a direction from the first tank toward the second branch portion.

3. The sterile sampling apparatus according to claim 1, wherein the first flow path further includes a first sterile connection connector.

4. The sterile sampling apparatus according to claim 1, wherein the first flow path further includes a sterilizing unit.

5. The sterile sampling apparatus according to claim 1, wherein the apparatus further includes a fluid identification sensor for identifying a fluid of the fifth flow path.

6. The sterile sampling apparatus according to claim 1, wherein the second flow path includes a second sterile connection connector.

7. The sterile sampling apparatus according to claim 1, wherein the second flow path which is upstream of the first opening/closing mechanism further includes an eighth flow path that branches off from the second flow path, and that communicates with a third tank for accommodating a buffer solution.

8. The sterile sampling apparatus according to claim 7, wherein the eighth flow path includes a third sterile connection connector.

9. The sterile sampling apparatus according to claim 1, wherein the sampling section includes a sample recovering section in which a container for recovering a sample that is ejected from a sample ejecting portion of the sampling section is to be disposed.

10. The sterile sampling apparatus according to claim 1, wherein the sampling section is disposed in a middle of the seventh flow path,
    wherein the sampling section includes a sample storing portion for storing a predetermined amount of the sample,
    wherein an end of the seventh flow path communicates with the ambient air, wherein the second pump is disposed between the sampling section and the end of the seventh flow path, wherein a ninth flow path is disposed between the sample storing portion and the sample ejecting portion, and wherein the ninth flow path includes a seventh opening/closing mechanism.

11. The sterile sampling apparatus according to claim 10, wherein the sampling section includes a level sensor that detects an amount of the sample which is stored in the sample storing portion.

12. The sterile sampling apparatus according to claim 1, wherein the sampling section is disposed in a middle of the seventh flow path, wherein the sampling section is a valve unit for storing a predetermined amount of the sample, wherein an end of the seventh flow path communicates with the ambient air, and wherein the second pump is disposed between the valve unit and the end of the seventh flow path.

13. The sterile sampling apparatus according to claim 1, wherein the sixth flow path includes a flow rate detecting unit.

* * * * *